(12) United States Patent
Streeper et al.

(10) Patent No.: US 11,918,555 B2
(45) Date of Patent: Mar. 5, 2024

(54) DICARBOXYLIC ACID ESTERS FOR THE TREATMENT OF DISEASES AND CONDITIONS ASSOCIATED WITH PHOSPHOLIPASE D TOXIN

(71) Applicant: NEW FRONTIER LABS, LLC, San Antonio, TX (US)

(72) Inventors: Robert T. Streeper, San Antonio, TX (US); Elzbieta Izbicka, San Antonio, TX (US)

(73) Assignee: NEW FRONTIER LABS, LLC, San Antonio, TX (US)

( * ) Notice: Subject to any disclaimer, the term of this patent is extended or adjusted under 35 U.S.C. 154(b) by 0 days.

(21) Appl. No.: 17/552,967

(22) Filed: Dec. 16, 2021

(65) Prior Publication Data

US 2022/0184024 A1 Jun. 16, 2022

Related U.S. Application Data

(60) Provisional application No. 63/126,374, filed on Dec. 16, 2020.

(51) Int. Cl.
*A61K 31/23* (2006.01)
*A61P 39/02* (2006.01)

(52) U.S. Cl.
CPC .............. *A61K 31/23* (2013.01); *A61P 39/02* (2018.01)

(58) Field of Classification Search
CPC .... A61K 31/23; A61K 31/225; A61K 9/0019; A61K 9/0053; A61K 2300/00; A61K 31/337; A61K 31/573; A61K 45/06; A61K 9/0014; A61P 43/00; A61P 3/10; A61P 3/08; A61P 17/10; A61P 25/00; A61P 29/00; A61P 3/00; A61P 31/04; A61P 31/12; A61P 35/00; A61P 37/02; A61P 9/10; A61P 29/02; A61P 3/06; A61P 39/02; Y02A 50/30
See application file for complete search history.

(56) References Cited

U.S. PATENT DOCUMENTS

| 2008/0044444 | A1  | 2/2008  | Tamarkin et al. |
| 2014/0094516 | A1* | 4/2014  | Streeper ................ A61P 31/12 |
|              |     |         | 435/375 |
| 2014/0296182 | A1  | 10/2014 | Levin et al. |
| 2016/0367533 | A1  | 12/2016 | Tambourgi et al. |

FOREIGN PATENT DOCUMENTS

JP 2007055988 A 3/2007

OTHER PUBLICATIONS

Lopes et al. (Frontiers in Pharmacology, May 2020, vol. 11, pp. 1-14) (Year: 2020).*

(Continued)

*Primary Examiner* — Savitha M Rao
(74) *Attorney, Agent, or Firm* — Pillsbury Winthrop Shaw Pittman LLP (57) ABSTRACT

The disclosure provides compositions and methods of treating diseases and conditions associated with phospholipase D (PLD) toxin. In particular, the methods include administering to a subject in need a pharmaceutical composition comprising a dicarboxylic acid ester.

12 Claims, 4 Drawing Sheets

(56) References Cited

OTHER PUBLICATIONS

Patent Cooperation Treaty, International Search Report and Written Opinion issued in PCT/IB2021/061874, dated Mar. 22, 2022, pp. 1-10.

Lajoie et al., "Phospholipase D Toxins of Brown Spider Venom Convert Lysophosphatidylcholine and Sphingomyelin to Cyclic Phosphates", PLOS ONE, Aug. 2013, pp. 1-7, vol. 8, Issue 8, e72372.

Albuquerque et al., Acute kidney injury due to systemic Loxoscelism: a cross-sectional study study in Northeast Brazil, Rev Soc Bras Med Trop, Sep.-Oct. 2008, pp. 695-699, vol. 51(5).

Arnold et al., "Brown Recluse Spider Envenomation", MEDSCAPE, Sep. 18, 2018, pp. 1-14.

Binford et al., "Molecular Evolution, Functional Variation, and Proposed Nomenclature of the Gene Family That Includes Sphingomyelinase D in Sicariid Spider Venoms", Mol. Biol. Evol., Nov. 28, 2008, pp. 547-566, vol. 26(3).

Cordes et al., "Evolutionary dynamics of origin and loss in the deep history of phospholipase D toxin genes", BMC Evolutionary Biology, 2018, pp. 1-19, vol. 18(194).

Du et al., "Phospholipase D2 Localizes to the Plasma Membrane and Regulates Angiotensin II Receptor Endocytosis", Molecular Biology of the Cell, Mar. 2004, pp. 1024-1030, pp. 1-7, vol. 15.

Dunbar et al., "The kiss of (cell) death: can venom-induced immune response contribute to dermal necrosis following arthropod envenomations?", Clinical Toxicology, Feb. 21, 2019, pp. 1-10.

Evans et al. "Ex Vivo Red Blood Cell Hemolysis Assay for the Evaluation of a pH-responsive Endosomolytic Agents for Cytosolic Delivery of Biomacromolecular Drugs", Journal of Visualized Experiments, Mar. 2013, pp. 1-5, vol. 73, e50166.

Gehrie et al., "Brown Recluse Spider Bite Mediated Hemolysis: Clinical Features, a Possible Role for Complement Inhibitor Therapy, and reduced RBC Surface Glycophorin A as a Potential Biomarker of Venom Exposure", PLOS ONE, Sep. 2013, pp. 1-10, vol. 8(9), e76558.

Gomez et al., "A New Assay for the Detection of Loxosceles Species (Brown Recluse) Spider Venom", Ann Emerg Med, May 2002, pp. 469-474, vol. 39(5).

Lajoie et al., "Phospholipase D Toxins of Brown Spider Venom Convert Lysophosphatidylcholine and Sphingomyelin to Cyclic Phosphates", PLOS ONE, Aug. 2013, pp. 1-7, vol. 8(8), e72372.

Lajoie et al., "Spider, bacterial and fungal phospholipase D toxins make cyclic phosphate products", Toxicon, 2015, pp. 176-180, vol. 108.

Lopes et al., "Targeting Loxosceles spider Sphingomyelinase D with small-molecule inhibitors as a potential therapeutic approach for loxoscelism", Journal of Enzyme Inhibition and Medicinal Chemistry, 2019, pp. 310-321, vol. 34(1).

McDade et al., "Brown Recluse Spider (*Loxosceles reclusa*) Envenomation Leading to Acute Hemolytic Anemia in Six Adolescents", The Journal of Pediatrics, 2010, pp. 155-157, vol. 156(1).

Mowry et al., 2014 Annual Report of the American Association of Poison Control Centers' National Poison Data System (NPDS): 32nd Annual Report, 2015, pp. 962-1146, vol. 53(10).

Paixao-Cavalcante et al., "Tetracycline Protects against Dermonecrosis Induced by Loxosceles Spider Venom", Journal of Investigative Dermatology, 2007, pp. 1410-1418, vol. 127.

Paludo et al., "Inflammatory events induced by brown spider venom and its recombinant dermonecrotic toxin: A pharmacological investigation", Comparative Biochemistry and Physiology, Part C, Nov. 13, 2008, pp. 323-333, vol. 149.

Pauli et al., "Analysis of therapeutic benefits of antivenin at different time intervals after experimental envenomation in rabbits by venom of the brown spider (*Loxosceles intermedia*)", Toxicon, Feb. 5, 2009, pp. 661-671, vol. 53.

Pezzi et al., "Spider Bite: A Rare Case of Acute Necrotic Arachnidism with Rapid and Fatal Evolution", Case Reports in Emergency Medicine, 2016, pp. 1-4, vol. 2016, Article ID 7640789.

Ribeiro et al., "Effects of copaiba oil on dermonecrosis induced by Loxosceles intermedia venom", Apr. 25, 2019, pp. 1-11, vol. 25:e149318.

Robinson et al., "Defining the complex phenotype of severe systemic loxoscelismusing a large electronic health record cohort", PLOS ONE, Apr. 19, 2017, pp. 1-15.

Rojas et al., "Phospholipase D from Loxosceles laeta Spider Venom Induces IL-6, IL-8, CXCL1/GRO-α, and CCL2/MCP-1 Production in Human Skin Fibroblasts and Stimulates Monocytes Migration", Toxins, Apr. 5, 2017, pp. 1-20, vol. 9(125).

Sams et al., "Necrotic arachnidism", J Am Acad Dermatol, Apr. 2001, pp. 561-576.

Selvy et al., "Phospholipase D—enzymology, functionality, and chemical modulation", Chem Rev., Oct. 12, 2011. pp. 6064-6119, vol. 111(10).

Streeper et al., "Oral Azelaic Acid Ester Decreases Markers of Insulin Resistance in Overweight Human Male Subjects", In Vivo, 2020, pp. 1-14, vol. 34.

Swanson et al., "Bites of Brown Recluse Spiders and Suspected Necrotic Arachnidism", The New England Journal of Medicine, Feb. 17, 2005, pp. 700-707, vol. 352.

Tambourgi et al., "Loxoscelism: From basic research to the proposal of new therapies", Toxicon, Feb. 6, 2010, pp. 1113-1119, vol. 56.

Tsukahara et al., "Phospholipase D2-Dependent Inhibition of the Nuclear Hormone Receptor PPARgamma by Cyclic Phosphatidic Acid", Mol Cell., Aug. 13, 2010, pp. 421-432, vol. 39(3).

Tsukahara et al., "Cyclic Phosphatidic Acid Decreases Proliferation and Survival of Colon Cancer Cells by Inhibiting Peroxisome Proliferator-Activated Receptor γ", Prostaglandins & Other Lipid Mediators, Oct. 2010, pp. 126-133, vol. 93(3-4).

Tsukahara et al., "Cyclic Phosphatidic Acid Influences the Expression and Regulation of Cyclic Nucleotide Phosphodiesterase 3B and Lipolysis in 3T3-L1 cells", Biochem Biophys Res Commun., Jan. 7, 2011, pp. 109-114, vol. 404(1).

Yang et al., "Transphosphatidylation by Phospholipase D*", The Journal of Biological Chemistry, Feb. 10, 1967, pp. 477-484, vol. 242(3).

Yi et al., "Necrotic Arachnidism and Intractable Pain From Recluse Spider Bites Treated With Lumbar Sympathetic Block", Clin J Pain, Jun. 2011, pp. 457-460, vol. 27(5).

\* cited by examiner

Fig. 1. Resolution of the brown recluse spider bite by topical DEA

Fig. 2. Quantitative analysis of the resolution of the brown recluse spider bite by topical DEA Fig. 4. DEA directly inhibits hemolytic activity of *L. reclusa* spider venom and recombinant phospholipase D from *L. intermedia*

PBS; phosphate buffered saline
DEA; diethyl azelate
LOX; *L. reclusa* spider venom
RBC; human red blood cells
rPLD; recombinant phospholipase D from *L. intermedia*

DICARBOXYLIC ACID ESTERS FOR THE TREATMENT OF DISEASES AND CONDITIONS ASSOCIATED WITH PHOSPHOLIPASE D TOXIN

RELATED APPLICATIONS

This patent application claims priority to U.S. Provisional Patent Application No. 63/126,374, filed Dec. 16, 2020, entitled "DICARBOXYLIC ACID ESTERS FOR THE TREATMENT OF DISEASES AND CONDITIONS ASSOCIATED WITH PHOSPHOLIPASE D TOXIN" naming inventors Robert T. STREEPER and Elzbieta IZBICKA. The entire content of the foregoing patent application is incorporated herein by reference.

FIELD OF THE INVENTION

The invention relates to methods and pharmaceutical compositions including dicarboxylic acid esters for treatment of diseases and conditions associated with phospholipase D toxin (PLD).

BACKGROUND

PLD toxins, also known as sphingomyelinases D (SMase D), are widespread in the animal kingdom. PLD belong to the protein domain family known as the GDPD-like SMase D/PLD. PLD can be found, for example, in venoms of spiders in the genera of *Loxosceles, Sicarius* and *Hexophthalma*, in scorpion venom, in tick saliva, and in exotoxins of pathogenic bacteria and fungi.

Among the PLD toxins, those of *loxosceles* spiders are the best characterized. Certain species of *loxosceles* have been associated with necrotic arachnidism (a hemolytic necrotic action) which is a cutaneous reaction to the venom, causing edema, skin necrosis, and ulcer formation at the envenomation site, known as cutaneous loxoscelism. Systemic effects of loxoscelism may further develop and occur in its mild form which includes nausea, vomiting, fever, chills, or arthralgia, myalgia, generalized rash, and in its more severe form which includes hemolysis, jaundice, rhabdomyolysis, circulatory shock, hemoglobinuria, intravascular coagulation, renal failure, coma, and in rare cases death.

Previous studies have shown that PLD toxin interacts with cell membranes of the envenomation victim triggering alterations which involve the complement system and activation of neutrophils resulting in the dermonecrotic skin lesions and systemic effects. (Pezzi et al., *Case Rep Emerg Med*, 2016, 7640789). PLD toxin acts as a potent endothelial cell agonist, inducing surface E-selectin expression and secretion of granulocyte macrophage colony-stimulating factor (GM-CSF) and interleukin-8 (IL-8/CXCL8) (Rojas, et al., *Toxins (Basel)*, 2017, 9(4):125; Tsukahara et al., *Mol Cell.* 2010, 39(3): 421-432). The enzymatic activity of PLD toxin is responsible for local and systemic effects. Histamine may potentiate the toxicity of venom PLD toxin and preheating venom significantly reduces toxicity (Paludo, et al., *Comp Biochem Physiol C Toxicol Pharmacol.* 2009, 149: 323-333). PLD toxin produces soluble choline and lipid cyclic phosphates that may act as neo-antigens (Lajoie et al., *PLoS One,* 2013, 8:e72372). Lipid cyclic phosphates are produced in transphosphatidylation of lysophosphatidic acid in which a free hydroxyl group within the substrate acts as an internal nucleophile (Yang, et al, *J Biol Chem,* 1967, 242:477-484). Bacterial, fungal and spider PLD toxin have been reported to produce pathogenically implicated lipid cyclic phosphates associated with lipid raft disruption (Lajoie et al., *Toxicon,* 2015, 108:176-180). Cyclic phosphatidic acid (1-acyl-2,3-cyclic-glycerophosphate), CPA, is generated in mammalian cells in a stimulus-coupled manner by the human PLD enzyme and binds to and inhibits the nuclear hormone receptor PPARγ with nanomolar affinity and high specificity. CPA has been proposed to act as a second messenger and a physiological inhibitor of PPARγ (Tsukahara et al., *Mol Cell.* 2010, 39(3): 421-432).

Confirmed cases of loxoscelism are relatively infrequent in the United States. Severe systemic loxoscelism in 57 cases over 20 years was associated with 3.5% mortality (Robinson, et al., *PLoS One,* 2017, 12, e0174941). Despite the evidence of low prevalence of moderate to severe cases of loxoscelism the potential for death or serious injury highlights the need for a treatment.

To date there are no approved drugs for loxocelism. An antiserum, available in Brazil, Argentina, Peru and Mexico, must be administered within 24 hours of envenomation (Pauli, et al., *Toxicon,* 2009, 53:660-671). Current efforts in drug development for loxoscelism include complement inhibitors (Gehrie et al, *PLoS One,* 2013, 8, e76558), natural oils (Ribeiro et al., *J Venom Anim Toxins Incl Trop Dis,* 2019, 25, e149318), small molecule inhibitors of PLD toxin (Lopes et al, *J Enzyme Inhib Med Chem,* 2019, 34:310-321), tetracycline (Paixao-Cavalcante et al., *J Invest Dermatol,* 2007, 127:1410-1418), and others (13).

Accordingly, there exists a need for methods of treating diseases, conditions or symptoms associated with PLD toxin.

SUMMARY OF THE INVENTION

In some aspects, embodiments herein relate to the use of dicarboxylic acid esters for treatment of diseases and conditions associated with PLD toxin.

In some aspects, embodiments herein relate to methods and pharmaceutical compositions including dicarboxylic acid esters for treatment of diseases and conditions associated with PLD toxin.

DESCRIPTION OF THE DRAWINGS

The following drawings demonstrate certain aspects of the present disclosure. The disclosure may be better understood by reference to one or more of these drawings in combination with the detailed description of specific embodiments presented herein.

Abbreviations: DEA; diethyl azelate, LOX; brown recluse *L.reclusa* spider venom, PBS; phosphate buffered saline, PLD toxin; phospholipase D, rPLD toxin; recombinant phospholipase D from *L.intermedia*, RBC; human red blood cells.

DETAILED DESCRIPTION

All applications, publications, patents and other references, cited herein are incorporated by reference in their entirety.

As used herein, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. As used herein, the term "about," is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, all numerical values or numerical ranges include integers within such ranges and fractions of the values or the integers within ranges unless the context clearly indicates otherwise. In addition, such ranges are also intended to include the numbers themselves and any sub-range between them. This range may be integral or continuous between and including the end values. Thus, for example, reference to a range of about 3 hours to about 10 hours, includes 3 hours, 4 hours, 5 hours, etc., as well as 3 hours and 1 minute, 3 hours and 2 minutes, 3 hours and 4 minutes, etc., 4 hours and 1 minute, 4 hours and 2 minutes, 4 hours and 4 minutes, etc. and so forth. Reference to a range of 90-100% includes 92.2% to 97.5%, 91.5 to 94.5, etc. Reference to a range of 1 to 25 days include sub-ranges from 1 day to 5 days, or from 3 days to 7 days, or from 5 days to 25 days.

As used herein, the term "comprising" is intended to mean that the pharmaceutical compositions (or compositions) and methods include the recited elements, but not excluding others. The term "consisting essentially of," as applied to the compositions of the present embodiments, means the composition can contain additional elements as long as the additional elements do not materially alter the composition. The term "materially altered," as applied to a composition, refers to an increase or decrease in the therapeutic effectiveness of the composition as compared to the effectiveness of a composition consisting of the recited elements. In other words, "consisting essentially of" when used to define compositions, shall mean excluding other components of any essential significance to the composition. Thus, a composition consisting essentially of the components as defined herein would not exclude trace contaminants from the isolation and purification method and pharmaceutically acceptable carriers. "Consisting of" shall mean excluding more than trace elements of other ingredients and substantial method steps for administering the compositions of this invention. Embodiments defined by each of these transition terms are within the scope of this invention.

As used herein, the term "optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used herein, the term "envenomation" refers to contact or injection of venom into a subject resulting from a bite, fang, tooth, or sting from a venomous carrier. The term "envenomation" also refers to injection from a venom delivery apparatus.

As used herein, the term "venom" refers to any poisonous or toxic substance which is subcutaneously, intramuscularly or topically transmitted, by the bite or sting or in contact of a venomous animal into a subject, which may contain various toxins such as, but not limited to, hemotoxins, cytotoxins, myotoxins, neurotoxins.

As used herein, the term "venomous carrier" refers to any animal or organism that produces, secrets, or carries a venom. Examples of venomous animals include, but are not limited to insect, reptile, amphibian, arthropod, mollusk, cnidarian, coelenterate or other venomous vertebrate or invertebrate animal. Examples of venomous organisms include, but are not limited to bacteria or fungi.

As used herein, a "subject" refers to a mammal such as a primate, in one embodiment as a human. Non-human primates include marmosets, monkeys, chimpanzees, gorillas, orangutans, and gibbons, to name a few. The term "subject" includes cats, dogs, ferret, chinchilla, mouse, rabbit, rat, gerbil, guinea pig, cattle, horses, pigs, sheep, goats, chickens, turkeys, ducks, pheasants, pigeons, doves, parrots, cockatoos, geese, etc.

As used herein, a "subject in need" of the methods of the disclosure can be a subject known to have, or suspected of having, or suspected of having a high probability of having any of the diseases and conditions disclosed herein that are associated with PLD toxin.

As used herein, the term "therapeutically effective" amount, refers to an amount that is sufficient to provide some improvement or benefit to the subject. Alternatively stated, a "therapeutically effective" amount is an amount that will provide some alleviation, mitigation, decrease, or stabilization in at least one clinical symptom in the subject. Those skilled in the art will appreciate that the therapeutic effects need not be complete or curative, as long as some benefit is provided to the subject. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The term "active ingredient" used herein refers to a biologically active substance. In embodiments, the dicarboxylic acid ester of the present disclosure is the active ingredient in a pharmaceutical composition. In embodiments, the dicarboxylic acid ester of the present disclosure is the only active ingredient in a pharmaceutical composition. In embodiments, the azelaic acid ester of the present disclosure is the active ingredient in a pharmaceutical composition. In embodiments, diethyl azelate is the active ingredient in a pharmaceutical composition.

As used herein, the term "pharmaceutically acceptable carrier" refers to any suitable adjuvants, carriers, excipients, or stabilizers, and can be in solid or liquid form such as, tablets, capsules, powders, solutions, suspensions, or emulsions, that does not cause significant irritation to the subject and does not abrogate the biological activity and properties of the administered active ingredients.

As used herein, the term "disease" is intended to be generally synonymous, and is used interchangeably with the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the term "dermonecrotic arachnidism" is intended to be generally synonymous, and is used interchangeably with the terms "necrotic arachnidism" or "necrosis" or "dermonecrosis" or "tissue necrosis," refers to the local skin and tissue injury as a result of envenomation or contact with PLD toxin.

As used herein, the term "skin ulcer" or "ulceration" refers to an open sore or wound on the skin wherein the epidermis is absent or otherwise compromised. The underlying dermis or hypodermis may be exposed and visible. The surrounding skin may be reddened and inflamed. The cardinal symptoms and signs of any kind of inflammatory process are pain, redness, heat, swelling, pain and loss of function. Such open sores may be prone to infection by pathogens such as bacteria, fungi, and viruses. In advanced cases, the sore may be oozing fluid-pus. Pus (dead immune cells, skin cells, subcutaneous tissue cells, cell fluid, and infectious agents) accumulate in the cavity of the skin ulcer to form an abscess.

As used herein, the "treating" or "treatment" of a disease or condition, may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combination thereof. Treatment may also mean a prophylactic or preventative treatment of a disease or condition.

As used herein, the term "inhibiting" refers to a decrease, reduction, limiting, and/or blocking of a particular action, function, interaction, appearance of a symptom. In embodiments, the term refers to reducing or preventing the level of certain activities, functions, interactions, appearances of certain symptoms (e.g., % hemolysis, % cytolysis, enzymatic activity, levels of biomarkers including but not limited to proteinaceous or non-proteinaceous molecules in tissues and body fluids, quantified images) in a subject to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. The measurable change may be objective (e.g., measurable by some test or marker, for example, in an in vitro or in vivo assay or test or observation, or subjective (e.g., the subject gives an indication of or feels an effect).

In embodiments, the disclosure provides a method of treating a subject suffering from a disease or condition associated with PLD toxin, including administering to a subject a pharmaceutical composition including a dicarboxylic acid ester having the Formula I: $R_2OOC-(CH_2)_n-COOR_1$. In embodiments, n is between 4 and 10, between 6 and 9, or between 7 and 8. In embodiments, each $R_1$ and $R_2$ are independently a lower alkyl. The term "lower alkyl," as used herein, refers to a C1 to C6 saturated straight or branched alkyl group. Example of suitable lower alkyl groups ($R_1$ and $R_2$) in Formula I include methyl, ethyl, propyl, isopropyl, butyl, sec-butyl, t-butyl, 1, 2 or 3 pentyl and the like groups. In embodiments, $R_1$ and $R_2$ are the same. In embodiments, $R_1$ and $R_2$ are the same. In embodiments, $R_1$ and $R_2$ are different.

In embodiments, the methods of the present disclosure comprise administering to a subject a therapeutically effective amount of a dicarboxylic acid ester of Formula I.

In embodiments, the dicarboxylic acid ester of Formula I is an azelaic acid ester. In embodiments, the azelaic acid ester is diethyl azelate, dimethyl azelate, or mixtures thereof. In embodiments, the azelaic acid ester is diethyl azelate.

The dicarboxylic acid ester may be obtained commercially or prepared by various methods known in the art. In embodiments, the dicarboxylic acid ester can be prepared via direct formation of the ester from the requisite acid and an alcohol. This condensation may be achieved by the dehydration of the reaction mixture with a suitable agent or by heating a mixture of the acid and alcohol. In embodiments, the dicarboxylic acid ester can be prepared by reacting an alcohol with an activated form of the acid. Activated forms of the acid include acid halides, acid anhydrides including both homo and hetero anhydrides, the reaction of the internal anhydride of the parent acid with the requisite alcohol, esters and anhydrides of both the acid and the alcohol which are formed by reaction of the requisite acid or alcohol with p-toluene sulfonyl chloride to produce the tosyl anhydride or ester which is subsequently reacted with the alcohol or acid respectively to produce the desired final ester. Similarly, one could substitute a simple organic acid anhydride, such as acetic acid anhydride, for the p-toluene sulfonyl chloride. In addition, one could start with one ester selected from among the desired compositions of matter and by the means of solution of the ester in a desired alcohol in the presence of an appropriate acidic or basic catalyst effect a conversion of the starting ester of the acid to an ester wherein the alcohol becomes that in which the reaction is carried out which method is also known to the art as trans-esterification.

For example, one could start with the dimethyl ester of the acid and by solution of the ester in ethanol in the presence of an acid or base one could cause the facile formation of the diethyl ester of the acid. In addition, if a mixed ester of the acid were desired, one could utilize an appropriately composed solution of the two or more desired alcohols in any of the methods herein described.

One could resort to the use of halogenated intermediates or ingredients to form the required esters. For example, thionyl chloride will chlorinate both acids and alcohols, thereby resulting in the acyl and alkyl chlorides. These acyl and alkyl chlorides may then be further reacted with the desired alcohol or acid respectively to produce the desired ester products. Other common halogenating agents include for example oxalyl chloride and the chlorides and bromides of phosphorous such as phosphorous penta or trichloride and penta or tribromide or phosphorous oxychloride.

Finally, it is commonly practiced to form esters through the action of a strong base on a mixture of the acid and the alcohol. Examples of strong bases include lithium aluminum hydride and other metal hydrides, alkali metal alkoxides such as sodium ethoxide and diisobutyl aluminum hydride and so on.

In embodiments, the disclosure provides a method of treating a subject suffering from a disease or condition associated with PLD toxin, includes administering to a subject a pharmaceutical composition including an azelaic acid ester. In embodiments, the disclosure provides a method of treating a subject suffering from a disease or condition associated with PLD activity, includes administering to a subject a pharmaceutical composition including diethyl azelate.

Source of Exposure to PLD Toxin

In embodiments, the disease or condition associated with PLD toxin is caused by exposure to PLD toxin. In embodiments, the subject is exposed to PLD toxin by envenomation of PLD toxin. In embodiments, the subject is exposed to PLD toxin via contact with an organism carrying PLD toxin.

In embodiments, the source of the envenomation of PLD is an Arthropod. Examples of Arthropods include families of organisms such as insects, arachnids, myriapods, and crustaceans.

In embodiments, the Arthropod includes the class Arachnida. Generally, Arachnids are spiders, harvestmen, mites, ticks, and scorpions. Arachnida is a class of joint-legged invertebrate animals in the subphylum Chelicerata. There are several orders within the arachinda, such as, for examples, Scorpions, Araneae, and Acari.

In embodiments, the class Arachinda includes the order Scorpions. In embodiments, the Scorpions include the family Buthidae (also known as buthid scorpions).

In embodiments, the class Arachinda includes order Araneae (spiders). Nearly all spiders have venom glands.

In embodiments, the order Araneae includes the family Sicariidae. Sicariidae is a family of six-eyed venomous spiders known for their potentially necrotic bites. The family Sicariidae includes three genera: *Hexophthalma, Loxosceles*, and *Sicarius*.

In embodiments, the family Sicariidae includes the genus *Hexophthalma*. Examples of species of *Hexophthalma* include *albospinosa, binfordae, damarensis, dolichocephala, goanikontesensis, hahni, leroyi*, and *spatulata*.

In embodiments, the family Sicariidae includes the genus *Loxosceles*. Examples of species of *Loxosceles* include *accepta, adelaida, alamosa, alicea, amazonica, anomala, apachea, aphrasta, aranea, arizonica, aurea, baja, barbara, belli, bentejui, bergeri, bettyae, blancasi, blanda, boneti, candela, carabobensis, cardosoi, caribbaea, carinhanha, carmena, cederbergensis, chapadensis, chinateca, colima, conococha, coquimbo, corozalensis, coyote, cubana, cubiroensis, curimaguensis, dejagerae, deserta, devia, diaguita, ericsoni, fontainei, foutadigalloni, francisca, frizzelli, gaucho, gloria, griffinae, guajira, guatemala, guayota, haddadi, harrietae, herreri, hirsuta, huasteca, hupalupa, immodesta, inca, insula, intermedia, irishi, jaca, jamaica, jarmila, julia, kaiba, karstica, lacroxi, lacta, laeta, lawrencei, lutea, luteola, mahan, maisi, makapanensis, malintzi, manuela, maraisi, martha, meruensis, misteca, mogote, mrazig, mulege, muriciensis, nahuana, neuvillei, iedeguidonae, olivaresi, olmea, pallalla, pallidecolorata, palma, panama, parramee, persica, pilosa, piura, pucara, puortoi, reclusa, rica, rosana, rothi, rufescens, rufipes, russelli, sabina, sansebastianensis, seri, similis, simillima, smithi, sonora, spadicea, speluncarum, spinulosa, surca, taeniopalpis, taino, tazarte, tehuana, tenango, teresa, tibicena, tlacolula, troglobia, valdosa, callenar, variegata, virgo, vonwredei, weyrauchi, willianilsoni, yucatana*, and *zapoteca*. In embodiments, the species of *Loxosceles* is *Loxosceles reclusa* which is also known as recluse spiders, brown recluse, fiddle-backs, violin spiders, and reapers.

In embodiments, the family Sicariidae includes the genus *Sicarius*. Examples of species of *Sicarius* include *andinus, boliviensis, cariri, crustosus, diadorim, fumosus, gracilis, Jequitinhonha, lanuginosus, levii, mapuche, ornatus, peruensis, rugosus, rupestris, saci, thomisoides, tropicus, utriformis, vallenato*, and *yurensis*.

In embodiments, the order Araneae includes the family Theridiidae. In embodiments, the family Theridiidae includes the genus *Latrodectus*. Examples of species of *Latrodectus* includes widow spiders, specific species of widow spiders include, such as, *Latrodectus mactans* (southern black widow), *Latrodectus Hesperus* (western black widow), *Latrodectus variolus* (northern black widow), *Latrodectus bishop* (Red Widow), *Latrodectus geometricus* (Brown Widow), *Latrodectus tredecimguttatus* (European black widow), *Latrodectus hasseltii* (Australian redback black widow), *Latrodectus corallinus* (American black widow), *Latrodectus curacaviensis* (American black widow), and button spiders (Southern Africa).

In embodiments, the Arachinda is order Acari. Order Acari includes, but is not limited to, ticks and mites.

In embodiments, the exposure to PLD toxin is caused by envenomation by ticks. More specifically, in embodiments, the exposure to PLD toxin is caused by contacting with tick saliva or injection of tick saliva into the subject. In embodiments, the source of tick saliva comes from *Ixodes* ticks.

In embodiments, the exposure to PLD toxin is caused by envenomation by mites or contacting with mites. In embodiments, the mites is predatory mites (*Metaseiulus*) or house dust mites (*Dermatophagiodes*).

In embodiments, the exposure to PLD toxin is caused by envenomation by a scorpion, a spider, ticks or mites.

In embodiments, the exposure to PLD toxin is caused via an organism which carries PLD toxin. Such organisms include, but are not limited to, for example pathogenic bacteria or pathogenic fungi. Examples of two genera of pathogenic bacteria include, but are not limited to, *Corynebacteria* and *Arcanobacterium* described in McNamara P J, et.al., Toxic phospholipases D of *Corynebacterium pseudotuberculosis, C. ulcerans* and *Arcanobacterium haemolyticum*: cloning and sequence homology; Gene (1995), 156(1): 113-8. Examples of pathogenic fungi include, but are not limited to, *Aspergillus* and *Coccidioides* described in Fry B G, et al., The toxicogenomic multiverse: convergent recruitment of proteins into animal venoms. Annu Rev Genomics Hum Genet (2009), 10: 483-511.

Loxoscelism

Local Toxicity: Cutaneous lesion in *Loxosceles* bites is characterized localized necrotic wound (necrosis) at the site of bite. A hemorrhagic, vesicular area is often surrounded by a perimeter of blanched skin, and commonly, erythema peripheral to this area. (Mueller et al., Mo. Med. 2014, 111(2): 139-142). The pathophysiology for this necrosis involves the cytotoxic effects of PLD toxin found in *Loxosceles* venom.

Systemic Toxicity: In addition to localized necrosis, some subjects may develop systemic effects of *loxosceles* envenomation (loxoscelism). Systemic symptoms of loxoscelism include fever and chills, nausea and vomiting, arthralgias, intravascular hemolysis with hemoglobinuria, rhabdomyolysis, disseminated intravascular coagulation (DIC) and acute kidney injury. (Repplinger, et al., Goldfrank's Toxicologic Emergencies, 11e New York, NY: McGraw-Hill). PLD toxin has also been implicated in systemic loxoscelism, damaging the erythrocyte cell membrane and recruiting inflammatory mediators leading to a systemic inflammatory reaction. (Kurpiewski et al., Platelet aggregation and sphingomyelinase D activity of a purified toxin from the venom of *Loxosceles reclusa*. Biochim Biophys Acta. 1981; 678: 467-476).

In embodiments, the methods and pharmaceutical compositions of the present disclosure are useful in the treatment of any disease and conditions associated with contacts of PLD toxin. The methods include administrating a pharmaceutical composition including azelaic acid esters to a subject in need. Such diseases, conditions, and symptoms may include necrotic arachnidism, viscerocutaneous arachnidisum, pain, erythema, ecchymosis, edema, dermonecrosis, ulcer formation, known as cutaneous loxoscelism. (Malaque et al., Rev. Inst. Med. Trop.S. Paulo, 2002, 44(3), On-line version ISSN 1678-9946).

In embodiments, the disclosure provides methods for prophylactic treatment of diseases and conditions associated with PLD toxin, includes administrating a pharmaceutical composition including a dicarboxylic acid ester of the present disclosure to a subject in need. In embodiments, the method includes administrating the pharmaceutical compositions prior to contacting with PLD toxin.

In embodiments, the disclosure provides methods for prophylactic treatment of a disease or a condition selected from necrotic arachnidism, viscerocutaneous arachnidisum, pain, erythema, ecchymosis, edema, dermonecrosis, ulcer formation, and combination thereof to a subject in need, includes administrating a pharmaceutical composition including a dicarboxylic acid ester of the present disclosure to the subject.

In embodiments, the disclosure provides methods for treating loxoscelism to a subject in need, includes administrating a pharmaceutical composition including a dicarboxylic acid ester of the present disclosure to the subject.

In embodiments, the disclosure provides methods for inhibiting cutaneous lesion, inhibiting tissue inflammation, inhibiting dermonecrosis, inhibiting hemolysis, inhibiting ulceration, inhibiting cytolysis, inhibiting hematological activities, inhibiting complement fixation to surfaces of mammalian cells, inhibiting compartment syndrome, inhibiting a biological toxicity associated with PLD toxin in a subject, includes administrating a pharmaceutical composition including a dicarboxylic acid ester of the present disclosure to a subject in need.

In embodiments, the disclosure provides methods for inhibiting dermonecrosis associated with PLD toxin in a subject, includes administrating a dicarboxylic acid ester of the present disclosure to the subject.

In embodiments, the disclosure provides methods for inhibiting hemolysis associated with PLD toxin in a subject, includes administrating a dicarboxylic acid ester of the present disclosure to the subject.

In embodiments, the disclosure provides methods for inhibiting ulceration associated with PLD toxin in a subject, includes administrating a dicarboxylic acid ester of the present disclosure to the subject.

In embodiments, the disclosure provides methods for inhibiting cytolysis associated with PLD toxin in a subject, includes administrating a dicarboxylic acid ester of the present disclosure to the subject.

In embodiments, the disclosure provides methods for inhibiting hematological activities associated with PLD toxin in a subject, includes administrating a dicarboxylic acid ester of the present disclosure to the subject.

In embodiments, the disclosure provides methods for inhibiting complement fixation to surfaces of mammalian cells associated with PLD toxin in a subject, includes administrating a dicarboxylic acid ester of the present disclosure to the subject.

In embodiments, the disclosure provides methods for inhibiting a biological toxicity associated with PLD toxin in a subject, includes administrating a dicarboxylic acid ester of the present disclosure to the subject.

In embodiments, the disclosure provides methods for inhibiting compartment syndrome, includes administrating a dicarboxylic acid ester of the present disclosure to the subject. Envenomation may cause compartment syndrome in a subject. Compartment syndrome occurs due to a vicious cycle of edema causing hypoxia and acidosis, which further increases capillary permeability and fluid extravasation. This results in a volume increase in the closed fascial compartment, which ultimately compromises circulation and causes irreversible muscle and nerve damage. (Dhar, Oman Med. J., 2015, 30(2): e082).

Tissue Responses

Upon envenomation, the subject/victim's epithelial and endothelial cells may be exposed to a venom that contains PLD toxin. These cells are capable of synthesizing and releasing a wide variety of chemokines and cytokines in response to a variety of stimuli. The release of chemokines and cytokines triggers additional events such as the attraction of neutrophils (a type of white blood cell) to the envenomation site. Some of the local skin reactions that are manifested as a result of envenomation include edema (excess liquid in tissue causes swelling) and erythema (skin redness) that are caused directly by constituents of the venom due to the hemolytic action of PLD toxin. It has been hypothesized that dermonecrosis may be due in part to an immune response.

In embodiments, the disclosure provides methods for preventing tissue responses elicited by PLD toxin, including administrating a pharmaceutical composition including a dicarboxylic acid ester of the present disclosure to a subject in need.

In embodiments, the disclosure provides methods for protecting mammalian cells from the activity of PLD toxin, including administrating a pharmaceutical composition including a dicarboxylic acid ester of the present disclosure to a subject in need.

In embodiments, the disclosure provides methods for reducing the pain responses secondary to envenomation, including administrating a pharmaceutical composition including a dicarboxylic acid ester of the present disclosure to a subject in need.

In embodiments, the disclosure provides the use of a dicarboxylic acid ester of the present disclosure in the manufacture of a medicament for topical, transdermal, intravenous, subcutaneous, intramuscular, oral, or parenteral delivery with the intention of relieving disease conditions in a subject. In embodiments, the disclosure provides the use of an azelaic acid ester of the present disclosure in the manufacture of a medicament for topical, transdermal, intravenous, subcutaneous, intramuscular, oral, or parenteral delivery with the intention of relieving disease conditions in a subject.

Methods of Administration

The pharmaceutical composition of the present disclosure may be administered to a subject in a variety of ways. For example, the pharmaceutical compositions can be administered topically, transdermally, intravenously, subcutaneously, intramuscularly or orally. The pharmaceutical composition may be applied locally at and/or around the envenomation site.

The treatment regime can vary depending upon various factors typically considered by one of ordinary skill in the art. These factors include the route of administration, the nature of the formulation, the nature of the patient's illness, the subject's size, weight, surface area, age, gender, other drugs being administered to the patient, and the judgment of the attending physician. The pharmaceutical compositions can be administered along with or in addition to other treatments for any of the diseases and conditions associated with PLD toxin.

The pharmaceutical compositions can be administered in combination with one or more additional therapeutic agents for the treatment of diseases and conditions associated with PLD toxin. The one or more additional therapeutic agents may be administered by the same or different routes of administration. The one or more additional therapeutic agents may include corticosteroids, dapsone, antibiotics, antifungals, pain relievers, and other antivenoms.

The pharmaceutical compositions can be administered to a subject immediately after exposure to PLD toxin or after envenomation, or about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein (such as, from about 1 minute to about 20 minute, or from about 3 hours to about 10 hours), after exposure to PLD toxin or after envenomation. The pharmaceutical compositions may be applied topically to an area of and/or around an envenomation site.

In embodiments, for prophylactic treatments, the pharmaceutical compositions can be administered to a subject at a time period of from 96 hours to immediately before, from 72 hours to immediately before, from 48 hours to immediately before, from 24 hours to immediately before, from 12 hours to immediately before, from 8 hours to immediately before, from 4 hours to immediately before, from 2 hours to immediately before, from 1 hour to immediately before, or from 0.5 hour to immediately before the subject is exposed to PLD toxin, or any range derivable therein immediately before the subject is exposed to PLD toxin. The pharmaceutical compositions may be applied topically to an area of healthy skin, at any time, for example, in one embodiment, before hiking.

The pharmaceutical compositions can be administered to a subject exposed to PLD toxin at about every 1 to about 24 hours, about every 1 to about 12 hours, about every 2 to about 8 hours, about every 2 to about 6 hours, about every 4 to about 6 hours, about every 4 to about 8 hours, about every 12 hours, about every 24 hours, about every 48 hours, or more often. In embodiments, the pharmaceutical composition can be administered once, twice, three times, four times, five times, six times, seven times, eight times, or more often daily. In embodiments, the pharmaceutical composition can also be administered daily, every other day, every two days, every three days, every four days, or less often, or any combination thereof. In embodiments, the pharmaceutical composition can be administered to a subject for a duration of from 1 day to 30 days, from 1 day to 25 days, from 1 day to 20 days, from 1 day to 15 days, or from 1 day to 10 days.

Formulations

In embodiments, the pharmaceutical compositions of the disclosure can be formulated for delivery via any route of administration known in the art, including but not limited to topical, transdermal, intravenous, subcutaneous, intramuscular, or oral administration.

Proper formulation is dependent upon the route of administration chosen. Any of the well-known techniques, carriers, and excipients as understood in the art may be used e.g., those disclosed in Remington's Pharmaceutical Sciences, 18th ed, (Mack Publishing Company: Easton, Pa., 1990) incorporated herein by reference. The pharmaceutical compositions disclosed herein may be manufactured in any manner known in the art, such as by means of conventional mixing, dissolving, granulating, levigating, emulsifying, encapsulating, entrapping or compression processes.

The pharmaceutical compositions include those suitable for topical, transdermal, intravenous, subcutaneous, intramuscular, or oral administration, although the most suitable route may depend upon, for example, the condition and disorder of the recipient.

In embodiments, the pharmaceutical composition is suitable for topical and transdermal administrations. Topical and transdermal administration of azelaic acid esters of the present disclosure can be in the form of a processed gel, cream, lotion, solution, ointment, suspension, or emulsion. These pharmaceutical compositions may further include one or more suitable excipient disclosed herein.

Parenteral administration, such as intravenous, subcutaneous, intramuscular administration of azelaic acid esters of the present disclosure can be in the form of solutions, suspensions, or emulsions. In one embodiment, these formulations are prepared in a saline solution. These pharmaceutical compositions may further include one or more suitable excipient disclosed herein.

In embodiments, the pharmaceutical composition is suitable for oral administration. The pharmaceutical compositions may conveniently be presented in unit dosage forms and may be prepared by any of the methods well known in the art of pharmacy. Typically, these methods include the step of mixing azelaic acid ester, and optionally any co-administered active ingredient, with the carrier which constitutes one or more accessory ingredients. In general, the pharmaceutical compositions are prepared by uniformly and intimately mixing the active ingredients with liquid carriers or finely divided solid carriers or both and then, as necessary, shaping the product into the desired composition. The pharmaceutical composition and any optional secondary active ingredient, suitable for oral administration may be presented as discrete units such as capsules, cachets or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion. The active ingredient(s) may also be presented as a bolus, electuary or paste. These pharmaceutical compositions may further include one or more suitable excipient disclosed herein.

Excipients

In embodiments, the pharmaceutical composition of the disclosure may further include one or more excipients. The excipient may include a carrier, for example, water-insoluble polysaccharide or oligosaccharide. Examples of carriers include, but are not limited to, cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof.

The excipient may include a thickening agent, for example, a water-soluble polysaccharide. Examples of thickening agents include, but are not limited to, hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof.

In embodiments, the pharmaceutical composition of the disclosure may further include one or more pharmaceutical excipients, for example ascorbic acid, EDTA dihydrate, glycerin, citric acid monohydrate, sodium citrate dihydrate, sodium benzoate, sodium propionate, 70% sorbitol solution, sucralose, FD&C Yellow #6, artificial flavor (e.g., artificial peppermint flavor, artificial fruit flavor), purified water, or any combination thereof.

In embodiments, the pharmaceutical composition of the disclosure may include a preservative, Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; benzoic acid, benzyl alcohol and sorbic acid and salts thereof.

In embodiments, the pharmaceutical composition of the disclosure may include one or more acceptable pH adjusting agents and/or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in a pharmaceutically acceptable range. In embodiments, the pH of the pharmaceutical composition of the disclosure may be from pH 4 to pH 7.5.

In embodiments, the pharmaceutical composition of the disclosure may include a sugar alcohol. Examples of sugar alcohols include, but are not limited to, mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof.

In embodiments, the pharmaceutical composition of the disclosure may include an additive. Examples of additives include, but not limited to, diluents, binders, surfactants, lubricants, glidants, coating materials, plasticizers, coloring agents, flavoring agents, or pharmaceutically inert materials. Examples of diluents include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like. Examples of binders include, for example, hydroxypropylcellulose, methylcellulose, hydroxypropylmethylcellulose (hydroxypropyl methylcellulose), povidone, dextrin, pullulane, hydroxypropyl starch, polyvinyl alcohol, scacia, agar, gelatin, tragacanth, macrogol and the like. Examples of surfactants include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol, quaternary ammonium salts (e.g., Benzyldimethyltetradecylammonium Chloride Hydrate, Benzethonium Chloride, Benzylcetyldimethylammonium Chloride Hydrate, Benzyldimethylstearylammonium Chloride Hydrate, Benzyldodecyldimethylammonium Chloride Dihydrate, Benzyldodecyldimethylammonium Bromide), and the like. Examples of lubricants include, for example, stearic acid, calcium stearate, magnesium stearate, talc and the like. Examples of glidants include, for example, dried aluminum hydroxide gel, magnesium silicate and the like. Examples of coating materials include, for example, hydroxypropylmethyl cellulose 2910, aminoalkyl methacrylate copolymer E, polyvinylacetal diethylaminoacetate, macrogol 6000, titanium oxide and the like. Examples of plasticizers include, for example, triethyl citrate, triacetin, macrogol 6000 and the like.

In embodiments, the pharmaceutical composition of the disclosure includes a dicarboxylic acid ester of the present disclosure and a pharmaceutical acceptable carrier. In embodiments, the pharmaceutical composition includes at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% dicarboxylic acid ester of Formula I based on the total weight of the formulation. In embodiments, the pharmaceutical composition includes an amount of from about 5% to about 100% by weight, from about 5% to about 95% by weight, from about 5% to about 90% by weight, from about 5% to about 85% by weight, from about 5% to about 80% by weight, from about 5% to about 75% by weight, from about 5% to about 70% by weight, from about 10% to about 100% by weight, from about 10% to about 95% by weight, from about 10% to about 90% by weight, from about 10% to about 85% by weight, from about 10% to about 80% by weight, from about 10% to about 75% by weight, from about 10% to about 70% by weight, from about 15% to about 100% by weight, from about 15% to about 95% by weight, from about 15% to about 90% by weight, from about 15% to about 85% by weight, from about 15% to about 80% by weight, from about 15% to about 75% by weight, from about 15% to about 70% by weight, from about 20% to about 100% by weight, from about 20% to about 95% by weight, from about 20% to about 90% by weight, from about 20% to about 85% by weight, from about 20% to about 80% by weight, from about 20% to about 75% by weight, from about 20% to about 70% by weight, from about 25% to about 100% by weight, from about 25% to about 95% by weight, from about 25% to about 90% by weight, from about 25% to about 85% by weight, from about 25% to about 80% by weight, from about 25% to about 75% by weight, from about 25% to about 70% by weight, from about 30% to about 100% by weight, from about 30% to about 95% by weight, from about 30% to about 90% by weight, from about 30% to about 85% by weight, from about 30% to about 80% by weight, from about 30% to about 75% by weight, from about 30% to about 70% by weight, from about 35% to about 100% by weight, from about 35% to about 95% by weight, from about 35% to about 90% by weight, from about 35% to about 85% by weight, from about 35% to about 80% by weight, from about 35% to about 75% by weight, from about 35% to about 70% by weight, from about 40% to about 100% by weight, from about 40% to about 95% by weight, from about 40% to about 90% by weight, from about 40% to about 85% by weight, from about 40% to about 80% by weight, from about 40% to about 75% by weight, from about 40% to about 70% by weight, from about 45% to about 100% by weight, from about 45% to about 95% by weight, from about 45% to about 90% by weight, from about 45% to about 85% by weight, from about 45% to about 80% by weight, from about 45% to about 75% by weight, from about 45% to about 70% by weight, from about 50% to about 100% by weight, from about 50% to about 95% by weight, from about 50% to about 90% by weight, from about 50% to about 85% by weight, from about 50% to about 80% by weight, from about 50% to about 75% by weight, from about 50% to about 70% by weight, from about 55% to about 100% by weight, from about 55% to about 95% by weight, from about 55% to about 90% by weight, from about 55% to about 85% by weight, from about 55% to about 80% by weight, from about 55% to about 75% by weight, from about 55% to about 70% by weight, from about 60% to about 100% by weight, from about 60% to about 95% by weight, from about 60% to about 90% by weight, from about 60% to about 85% by weight, from about 60% to about 80% by weight, from about 60% to about 75% by weight, from about 60% to about 70% by weight of dicarboxylic acid ester of Formula I based on the total weight of the formulation.

In embodiments, the pharmaceutical composition of the disclosure includes a dicarboxylic acid ester of the present disclosure may be formulated and incorporated into all pharmaceutical dosage forms known to those skilled in the art. Such pharmaceutical compositions may be used in cells, tissues and organs of a subject in need of the treatment and to be administered over a wide range of doses. In embodiments, azelaic acid esters of the disclosure may be administered to the subject orally, parenterally, topically and locally, in a daily dosage of 0.001 mg/kg to 1000 mg/kg body weight per day.

Kits

In embodiments, the disclosure also provides a kit that includes a pharmaceutical composition of the present disclosure, especially for topical administration, a wipe to clean the site, a swab or brush to spread the applied material, an adhesive dressing to cover the site; optionally, the kit may include a disposal bag or container; optionally, the kit may include an absorbent element; optionally, the kit may include a pair of gloves (e.g., sterile nitrile or latex gloves).

EXAMPLES

Materials and Methods

Lyophilized *Loxosceles reclusa* venom (LOX) was purchased from SpiderPharm, Yarnell, AZ Immediately prior to the assay LOX was reconstituted in 20% glycerol in PBS. Recombinant *Loxosceles intermedia* Phospholipase D LiSicTox-alphaIA1a full length protein expressed in *E.coli* (part #MBS1258368), further referred to as rPLD toxin, was purchased from MyBiosource Inc, San Diego, CA Diethyl azelate (>99% purity) was prepared as described in Streeper, el al.,"Oral Azelaic Acid Ester Decreases Markers Of Insulin Resistance In Overweight Male Human Subjects." In Vivo (2020), 34(3), 1173-1186.

Topical Diethyl Azelate (DEA) Treatment of Brown Recluse Spider Bite

An adult male subject was bitten once on his left forearm, and twice on his neck about one year later. Diethyl azelate was applied topically to the envenomation site at approximately 4 to 8 hour intervals for 14 days. Progression of the treatment was documented by photography as shown in FIG. 1. Images of the affected neck area were normalized to the same size and converted to JPEG files. Inflamed red areas surrounding the bites visible as elevated lesions were outlined on the images and quantified using ImageJ software version 1.53e (ImageJ.nih.gov).

Hemolysis Assay

Hemolytic activity was assessed on human RBC. The assay using human erythrocytes followed an established procedure as described in Evans, et al., "Ex vivo red blood cell hemolysis assay for the evaluation of pH-responsive endosomolytic agents for cytosolic delivery of biomacromolecular drugs," *J Vis Exp,* 2013, e50166. Briefly, whole peripheral blood was drawn directly into K2-EDTA coated Vacutainer tubes and centrifuged at 500×g (relative centrifugal force). Pelleted erythrocytes were washed twice each with 150 mM NaCl and with phosphate buffered saline (PBS) and then reconstituted in 50-fold excess PBS. Immediately prior to the assay LOX was reconstituted in 20% glycerol in PBS. rPLD toxin was supplied as frozen stock in 10 mM Tris-HCl, 1 mM EDTA, 20% glycerol, was thawed on ice. The lysis assay was performed in 96-wells in a total volume of 200 ul. LOX and PLD toxin were and added as 20× concentrated stocks to the erythrocyte suspension. Triton X-100 (5% in serial dilutions to 0.04%) was used as a positive control. Incubation was performed for 60 min and the absorbance at 400 nm was measured using Tecan GENios microwell plate reader. Measurements were performed in triplicate repeats.

RESULTS AND DISCUSSION

Diethyl Azelate Resolves Consequences of Bites to a Human

The adult male subject suffered two incidents of brown recluse spider bite. In the first incident, the bite occurred to the forearm and the treatment was initiated 4 hours after envenomation. During the course of the treatment, the initially painless wound area began to swell, become warm and began to ache. By second day the arm had was approximately twice the pre-bite circumference and was mildly uncomfortable. By the fourth day the swelling and discomfort had largely subsided.

Approximately one year after the first incident the adult male subject suffered two recluse bites to the back of his neck. The treatment was initiated immediately after the bite.

Figure 1:
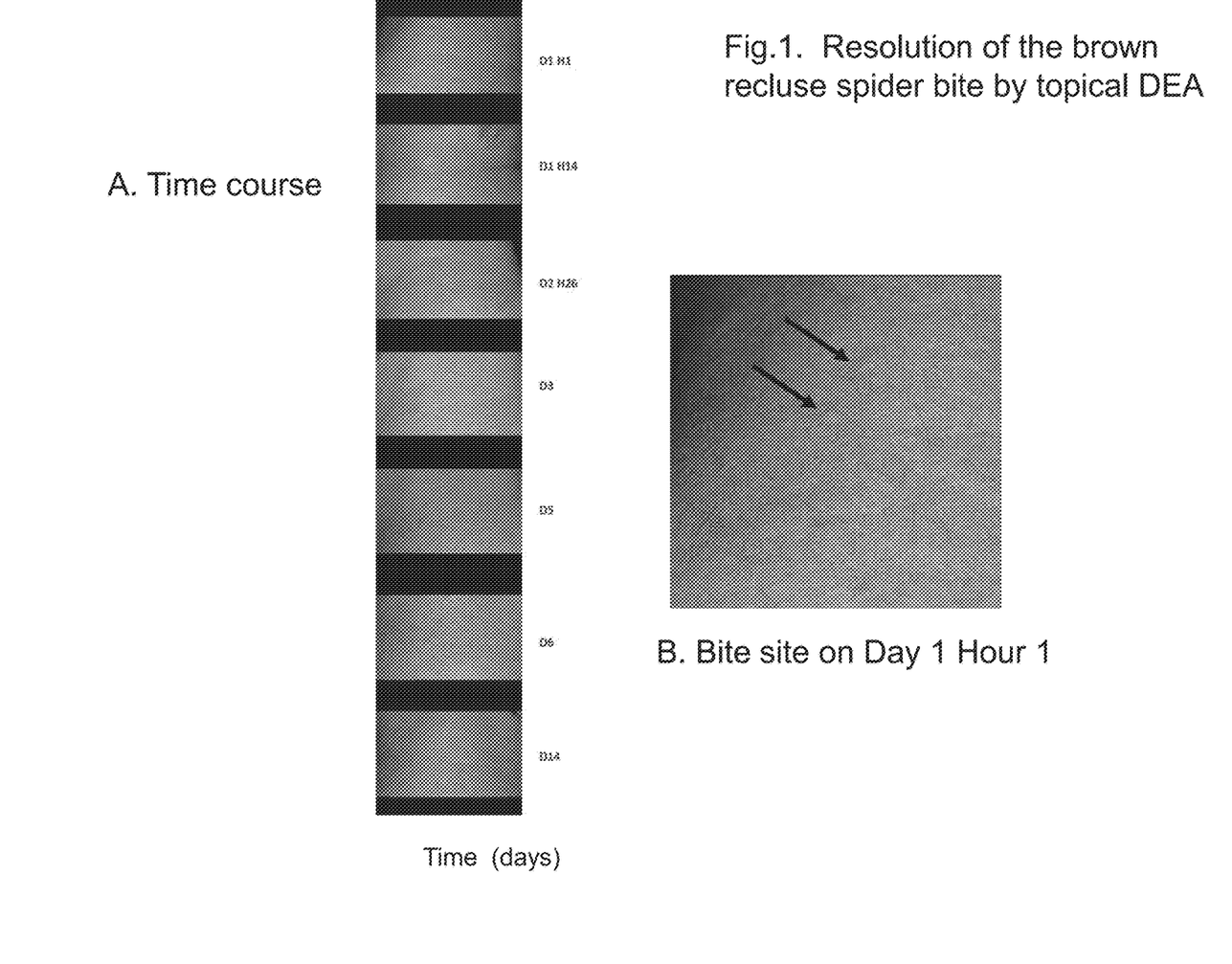
FIG. 1 shows photographs of a time-dependent resolution of a brown recluse spider bite over a treatment course with topical diethyl azelate (Image A) and a magnified image of the bite (Image B) according to certain embodiments of the present disclosure.

Representative images of the neck taken over the course of 14 days are shown in FIG. 1 (Image A). The top image labeled as "D1 H1" was taken on day one (hence "D1") after the first hour (hence "H1") after the bite; the second image labeled as "D1 H14" was taken on day one (hence "D1") after the first 14 hours (hence "H14") after the bite; and so on. A magnified image of the bite area with two bite sites indicated by arrows is shown in FIG. 1 (Image B). The inflamed red area around the two sites of the bite on the neck increased rapidly as shown on the first recorded image at 1-hour post-bite reaching the maximum on Day 2 at 26 hours post-bite. From that time point there was a gradual decrease of the redness, pain and swelling that was entirely resolved by Day 14.

Figure 2:
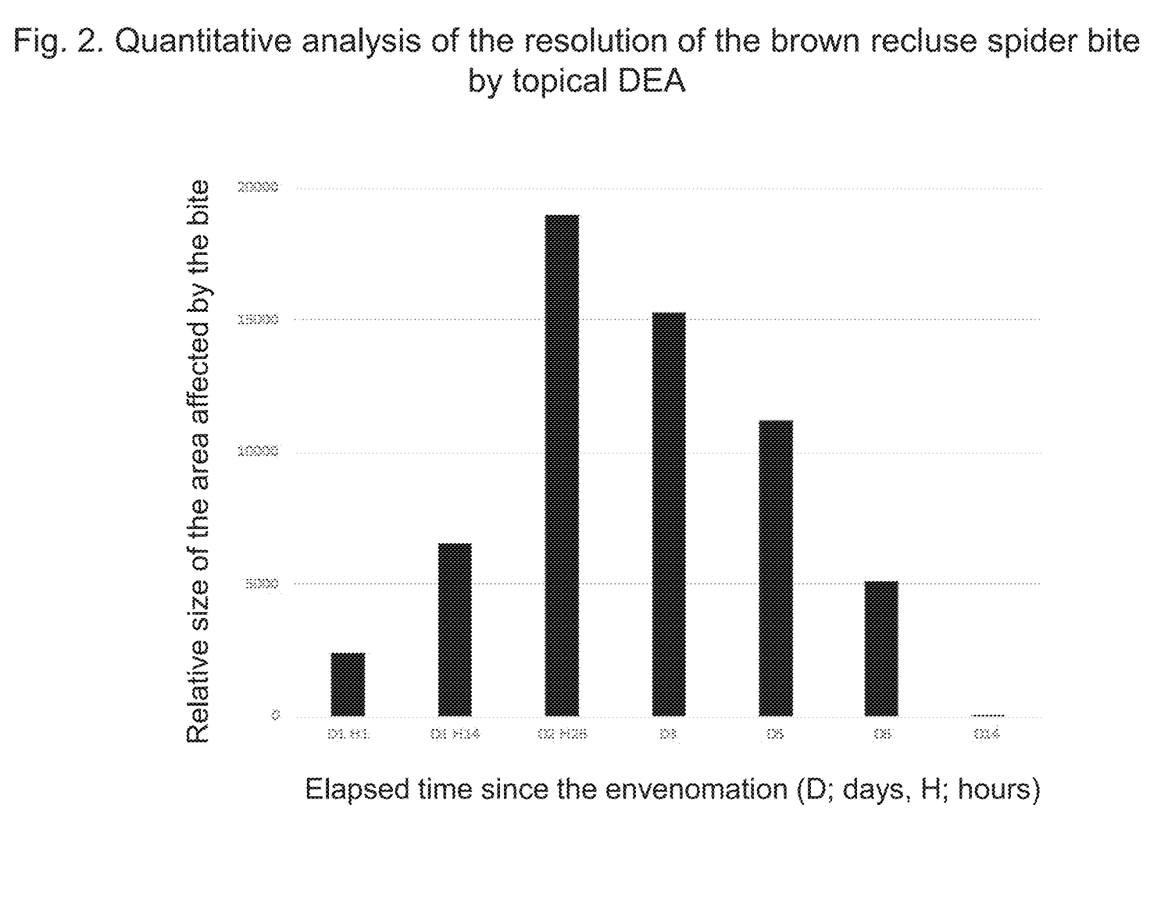
FIG. 2 is a quantitative analysis of the affected bite area over a treatment course with topical diethyl azelate according to certain embodiments of the present disclosure.

FIG. 2 is a bar chart illustrating the relative size of the area of arm affected by the brown recluse spider bite over the treatment course with topical DEA of 14 days. The x-axis shows the elapsed time since the envenomation event in days and hours as applicable.

Diethyl Azelate (DEA) Inhibits Hemolysis Induced by *L. Reclusa* Venom and by Recombinant PLD Toxin from *L. Intermedia*

Figure 4:
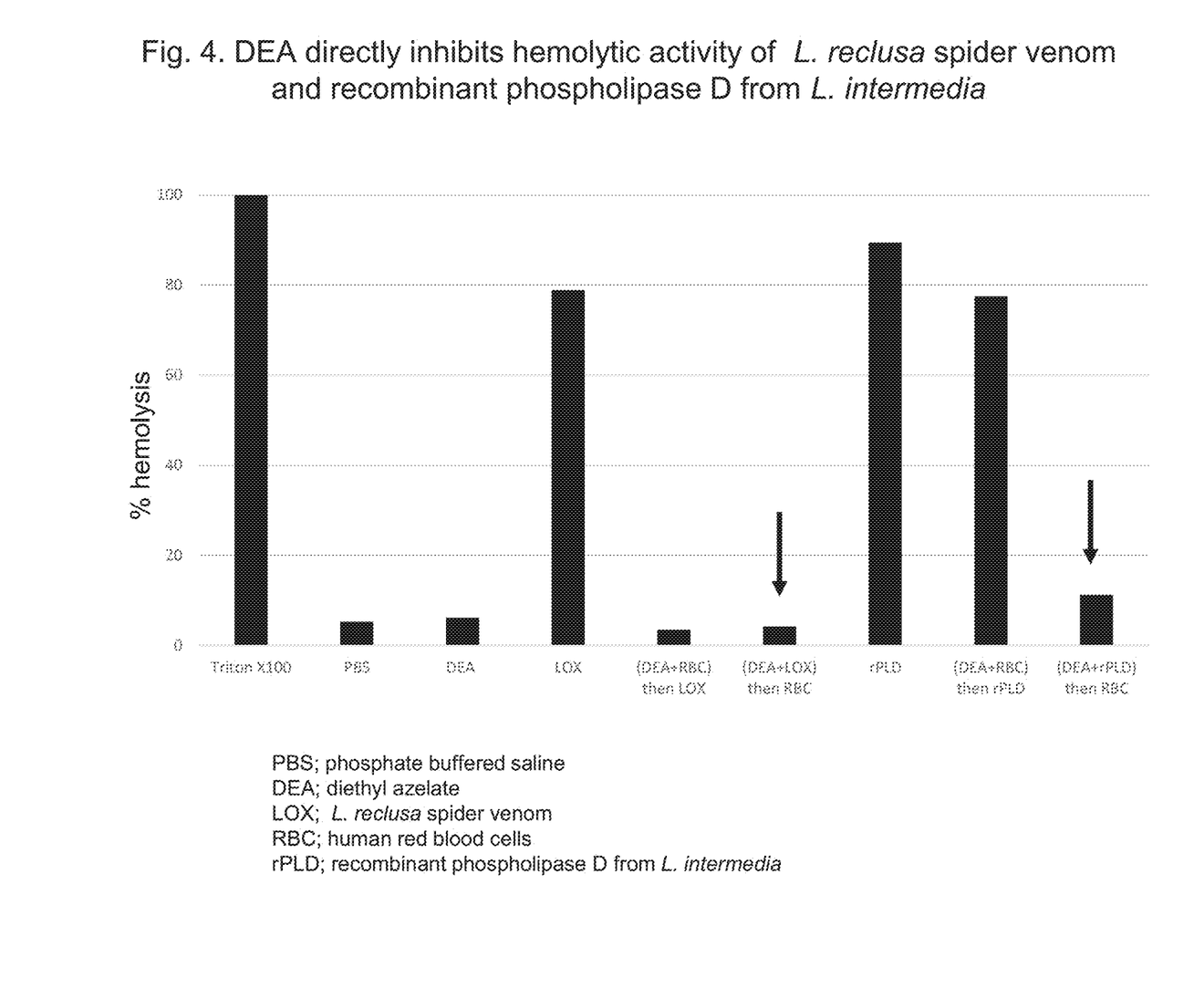

Human erythrocytes incubated with 5% Triton X100 were >95% hydrolyzed while those incubated with PBS or 122 µM DEA had no effect on hemolysis. The optical density at 400 nm of the erythrocyte solution in the presence of DEA was defined as a negative control. When LOX (75 µg/ml) was added to the erythrocyte suspension, the extent of hemolysis was 78%. On the other hand, preincubation of DEA with erythrocytes for 60 min followed by the addition of LOX, or preincubation of DEA with LOX for 60 min followed by the addition of erythrocytes also resulted in the inhibition of hemolysis as shown in FIG. 4.

Figure 3:
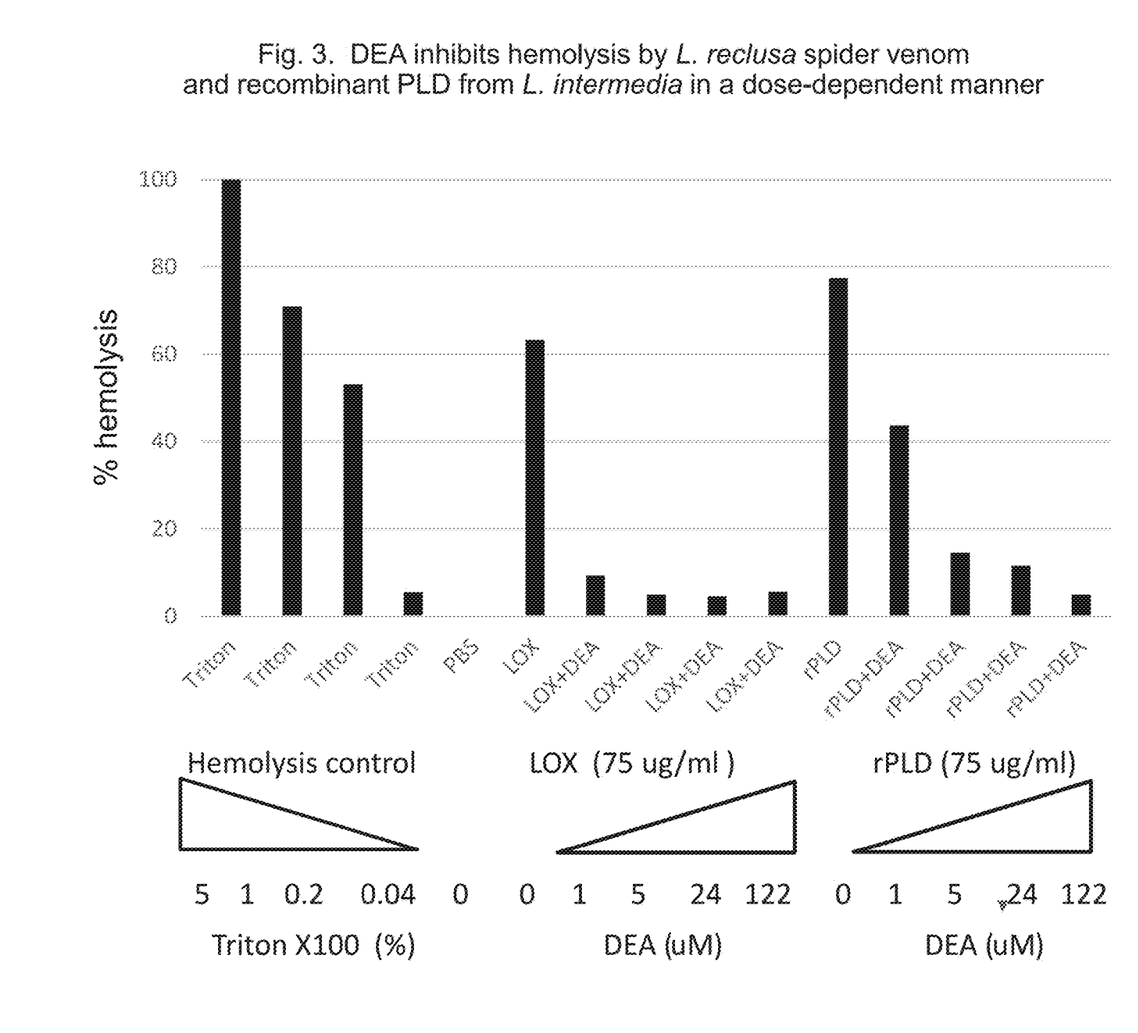
FIG. 3 demonstrates that DEA inhibits hemolysis by *L. reclusa* brown recluse spider venom and recombinant *L. intermedia* (rPLD toxin) in a dose-dependent manner FIG. 4 demonstrates that DEA directly inhibits enzymatic activity of PLD toxin as measured by hemolysis induced by *L. reclusa* spider venom and recombinant *L. intermedia* rPLD toxin.

FIG. 3 illustrates the effect of diethyl azelate in the presence of constant protein concentrations of rPLD toxin and LOX on RBC hemolysis in a dose-dependent manner. Dose effect of Triton X100 on the hemolysis is compared to that of DEA in the presence of constant protein concentrations of rPLD toxin and LOX. The results show that DEA significantly inhibits hemolysis in the presence of LOX starting at the lowest concentration of 1 µM DEA; DEA reduces hemolysis from 78% to 43% in the presence of PLD toxin starting at 1 µM DEA and continues to reduce hemolysis to well below 20% (specifically, to 16% at 5 µM DEA, to 13% at 24 µM DEA, and to 5% at 122 µM DEA).

What is claimed is:

1. A method of treating a human suffering from a disease or condition associated with phospholipase D toxin (PLD) by inhibiting one or more conditions selected from the group consisting of cutaneous lesion, tissue inflammation, dermonecrosis, hemolysis, ulceration, cytolysis, hematological activities, complement fixation to surfaces of mammalian cells, compartment syndrome, and a biological toxicity, comprising administering to the subject a pharmaceutical composition comprises from about 40% to about 100% by weight of diethyl azelate.

2. The method of claim 1, wherein the disease or condition associated with PLD toxin is caused by exposure to PLD toxin via envenomation or contact with an organism carrying PLD toxin.

3. The method of claim 2, wherein the source of the envenomation is an arthropod.

4. The method of claim 2, wherein the arthropod is an Arachnida or an Acari.

5. The method of claim 3, wherein the arthropod is selected from the group consisting of a scorpion, a spider, ticks and mites.

6. The method of claim 1, wherein the disease or condition is loxoscelism.

7. The method of claim 1, wherein the disease or condition is selected from the group consisting of necrotic arachnidism, viscerocutaneous arachnidisum, pain, erythema, ecchymosis, edema, dermonecrosis, ulcer formation, and combinations thereof.

8. The method of claim 1, wherein administering is performed topically, transdermal, subcutaneously, intramuscularly, intravenously, orally, or combinations thereof.

9. The method of claim 1, wherein the administering is performed topically.

10. The method of claim 1, wherein the administering is performed at about every 4 to about 8 hours.

11. The method of claim 1, wherein the administering is for a duration of from 1 day to 30 days.

12. The method of claim 1, for inhibiting hemolysis.

* * * * *